US008968791B2

(12) United States Patent
Moore et al.

(10) Patent No.: US 8,968,791 B2
(45) Date of Patent: Mar. 3, 2015

(54) DIETARY SUPPLEMENTS FOR PROMOTION OF GROWTH, REPAIR, AND MAINTENANCE OF BONE AND JOINTS

(75) Inventors: Jeremy D. Moore, O'Fallon, MO (US); Thomas R. Hampton, Wentzville, MO (US); Robert Harrell, Troy, MO (US)

(73) Assignee: Novus International, Inc., St. Charles, MO (US)

( * ) Notice: Subject to any disclaimer, the term of this patent is extended or adjusted under 35 U.S.C. 154(b) by 982 days.

(21) Appl. No.: 13/003,388

(22) PCT Filed: May 30, 2008

(86) PCT No.: PCT/US2008/065219
§ 371 (c)(1),
(2), (4) Date: Mar. 23, 2011

(87) PCT Pub. No.: WO2008/154178
PCT Pub. Date: Dec. 18, 2008

(65) Prior Publication Data
US 2011/0171187 A1  Jul. 14, 2011

Related U.S. Application Data

(60) Provisional application No. 60/942,281, filed on Jun. 6, 2007.

(51) Int. Cl.
*A61K 45/06* (2006.01)
*A23L 1/30* (2006.01)
*A23L 1/305* (2006.01)
*A23L 1/304* (2006.01)
*A23L 1/302* (2006.01)
*A61P 19/02* (2006.01)

(52) U.S. Cl.
CPC . *A61K 45/06* (2013.01); *A23L 1/30* (2013.01); *A23L 1/3008* (2013.01); *A23L 1/3016* (2013.01); *A23L 1/302* (2013.01); *A23L 1/3045* (2013.01); *A23L 1/305* (2013.01); *A23L 1/3051* (2013.01)
USPC ........... 424/581; 424/638; 424/641; 424/639; 424/442; 514/562; 514/492; 514/494; 514/500; 562/557; 562/559

(58) Field of Classification Search
CPC ............. A23L 1/32; A23L 1/30; A23L 1/302; A23L 1/3045; A23L 1/3051; C08L 1/00; C08L 5/00; A23K 1/00; A61K 35/12; A61K 35/54; A61K 31/19; A61K 31/315; A61K 45/06
USPC .......... 424/581, 638, 639, 641, 442; 514/562, 514/492, 494, 500
See application file for complete search history.

(56) References Cited

U.S. PATENT DOCUMENTS

| 4,335,257 | A | 6/1982 | Cummins et al. |
|---|---|---|---|
| 4,579,962 | A | 4/1986 | Takano |
| 4,851,226 | A | 7/1989 | Julian et al. |
| 5,075,114 | A | 12/1991 | Roche |
| 5,364,845 | A | 11/1994 | Henderson |
| 5,587,363 | A | 12/1996 | Henderson |
| 5,876,759 | A | 3/1999 | Gowan |
| 6,255,295 | B1 | 7/2001 | Henderson et al. |
| 6,476,005 | B1 | 11/2002 | Petito et al. |
| 6,492,349 | B1 | 12/2002 | Henderson |
| 6,583,123 | B2 | 6/2003 | Henderson et al. |
| 6,726,941 | B2 | 4/2004 | Ethington et al. |
| 6,924,273 | B2 | 8/2005 | Pierce |
| 7,029,703 | B2 | 4/2006 | Krumhar et al. |
| 2002/0025921 | A1 | 2/2002 | Petito et al. |
| 2002/0032169 | A1 | 3/2002 | Henderson et al. |
| 2002/0068718 | A1 | 6/2002 | Pierce |
| 2003/0034993 | A1 | 2/2003 | Baker et al. |
| 2003/0212005 | A1 | 11/2003 | Petito et al. |
| 2003/0216348 | A1 | 11/2003 | Henderson et al. |
| 2004/0170669 | A1* | 9/2004 | Kunkle et al. ................. 424/442 |
| 2004/0180025 | A1 | 9/2004 | Long et al. |
| 2005/0018022 | A1 | 1/2005 | Studer et al. |
| 2005/0113287 | A1 | 5/2005 | Nelson |
| 2005/0180025 | A1 | 8/2005 | Orimo et al. |
| 2005/0250849 | A1 | 11/2005 | Lorbert et al. |
| 2006/0292250 | A1 | 12/2006 | Giampapa |
| 2007/0010583 | A1* | 1/2007 | Dibner et al. ................. 514/557 |
| 2011/0171187 | A1 | 7/2011 | Moore |

FOREIGN PATENT DOCUMENTS

| EP | 1118332 | A1 | 7/2001 |
|---|---|---|---|
| WO | 9827988 | A1 | 7/1998 |
| WO | 9962524 | A1 | 12/1999 |
| WO | 2006012492 | A2 | 2/2006 |

(Continued)

OTHER PUBLICATIONS

English translation sent by our foreign associate on Mar. 30, 2012 of the Notification to Grant Patent Right issued Mar. 2, 2012 in related Chinese application No. 200880100351.2.
International Search Report and Written Opinion from related International application No. PCT/US12/20638, mailed May 4, 2012, 6 pages.
Wedekind, Efficacy of Steadfast(R) Equine joint supplement in a chemically-induced osteoarthritis rat model, The Journal of the Federation of American Societies for Experimental Biology, Apr. 2010, vol. 24, Meeting Abstracts Is, No. 726.5, 1 page.
Dierenfeld, Evaluation of a nutraceutical joint supplement in camels, 6th European Zoo Nutrition Conference, Barcelona 2010 [online], p. 37 [retrieved on Apr. 20, 2012 from the internet: <URL http://www.eaza.net/activities/Pages/Nutrition.aspx], 61 pages.

(Continued)

*Primary Examiner* — Sreeni Padmanabhan
*Assistant Examiner* — Irina Neagu
(74) *Attorney, Agent, or Firm* — Polsinelli PC

(57) ABSTRACT

The present invention provides a dietary supplement that promote the growth, repair, and maintenance of mammalian bone and joint connective tissue. In particular, the dietary supplement comprises a combination of at least one metal chelate and at least one chondroprotective agent.

24 Claims, No Drawings

(56) References Cited

FOREIGN PATENT DOCUMENTS

| WO | 2007001700 A2 | 1/2007 |
|---|---|---|
| WO | 2012096883 A1 | 7/2012 |

OTHER PUBLICATIONS

Taiwanese Office action and Search Report for Patent application No. 097121297 completed Jun. 21, 2013.
International Search Report, from PCT/US2008/0652 dated Aug. 15, 2008, 8 pages.
Novus, Comparing Supplemental Methionine Sources. Aliment, MFP, dated Dec. 13, 2007, 2 pages.
Ameye LG, Young MF. 2006. Animal models of osteoarthritis: lessons learned while seeking the 'Holy Grail'. Curr Opin Rheumatol. 18:537-547.
Bove SE, Calcaterra SL, Brooker RM, Huber CM, Guzman RE, Juneau PL, Schrier DJ, Kilgore KS. 2003. Weight bearing as a measure of disease progression and efficacy of anti-inflammatory compounds in a model of monosodium iodoacetate-induced3 osteoarthritis. Osteoarthritis and Cartilage 11:821-830.
Budsberg, Long term temporal evaluation of ground reaction forces during development of experimentally induced osteoarthritis in dogs, AJVR, vol. 62, No. 8 2001.
Garnero P. 2006. Use of biochemical markers to study and follow patients with osteoarthritis. Current Rheumatology Reports 8:37-44.
Gregory PJ, Sperry M, Friedman, Wilson A. 2008. Dietary supplements for arthritis. American Academy of Family Physicians 77:177-184.
Guincamp C, Gegout-Pottie P, Philippe L, Terlain B, Netter P, Gillet P. 1997. Mono-iodoacetate-induced experimental osteoarthritis. Arthritis & Rheumatism 40:1670-1679.
Hoffer LJ, Kaplan LN, Harnadeh MJ, et al. 2001. Sulfate could mediate the therapeutic effect of glucosamine sulfate. Metabolism 50:767-770.
McAlington TE. 2006. Nutraceuticals: do they work and when should we use them? Best Practice and Research Clinical Rheumatology. 20:99-115.
Verbruggen G. 2006. Chondroprotective drugs in degenerative joint diseases. Rheumatology 45:129-138.

* cited by examiner

DIETARY SUPPLEMENTS FOR PROMOTION OF GROWTH, REPAIR, AND MAINTENANCE OF BONE AND JOINTS

FIELD OF THE INVENTION

The present invention relates to dietary supplements that promote the growth, repair, and maintenance of mammalian bone and joint connective tissue.

BACKGROUND OF THE INVENTION

Approximately 40 million Americans suffer from significant levels of joint stiffness and pain. This stiffness or pain can stem from the cumulative effects of chronic mechanical stress experienced during strenuous athletic activities such as running or swimming. In addition, joint pain may be the result of traumatic injuries such as sprains, dislocations and fractures. Joint pain may also be due to the long-term effects of arthritic diseases such as osteoarthritis and rheumatoid arthritis. Besides pain in the joints, many of the joint conditions described above can result in disfigurement and loss of mobility. Approximately 6.9 million Americans have some sort of work limitation that is directly attributable to arthritis.

Treatments for joint pain depend upon its cause and severity. For relatively mild joint pain brought on by repetitive mechanical stress, reducing the stress by adjusting the intensity or duration of exercise, or using different footwear or supportive appliances is the simplest option, although this may not be appropriate for athletes or performance animals. For more severe joint pain, over-the-counter non-steroidal anti-inflammatory drugs (NSAIDs) such as ibuprofen (Advil, Motrin) and naproxen sodium (Aleve) can be helpful. In more severe cases, steroids such as prednisone or cortisone bring relief, although accompanied by a host of potential side effects such as weight gain, high blood pressure, and facial swelling. In the case of chronic arthritic conditions such as rheumatoid arthritis, other drugs such as etanercept or adulimumab that disrupt the immune system's inflammatory reaction are effective, but are also accompanied by side effects related to the disruption of the immune system. As a last resort, surgical interventions such as cartilage transplants or joint replacements can reduce symptoms. All of the above treatments may address the pain and limit further damage to the joints, but do little to facilitate the repair of joint tissues.

Another approach to treating joint pain is through the use of nutritional supplements that stimulate the growth, repair and maintenance of bone and joint connective tissue. One class of supplements is comprised of components of joint connective tissue: collagen, glucosamine, hyaluronic acid, and chondroitin. Other supplements act as catalysts or supply raw materials for bone and connective tissue synthesis: S-adenosylmethionione (SAM), methylsulfonylmethane (MSM), and other vitamins and minerals such as Vitamin C, manganese, magnesium, zinc, calcium, iron, and Vitamin B12. While some of these supplements provide some relief, they typically only address a limited subset of nutritional issues that impact overall joint health. A need therefore exists for a nutritional supplement that can be utilized to improve overall joint health.

SUMMARY OF THE INVENTION

Among the various aspects of the invention is one aspect that provides a dietary supplement. The dietary supplement comprises at least one chondroprotective agent and at least one metal chelate, wherein the metal chelate comprises at least one metal ion and at least one ligand, with the ligand comprising a compound having formula (1):

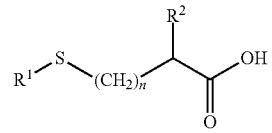

wherein:
  n is an integer from 0 to 2;
  $R^1$ is methyl or ethyl; and
  $R^2$ is selected from the group consisting of hydroxyl and amino.

Another aspect of the invention encompasses a method for promoting at least one of pain relief, growth, repair, and/or maintenance of bone and/or joint tissue in a mammalian subject. The method comprises administering to the mammalian subject a dietary supplement comprising at least one chondroprotective agent and at least one metal chelate. The metal chelate comprises at least one metal ion and at least one ligand, wherein the ligand comprises a compound having formula (1):

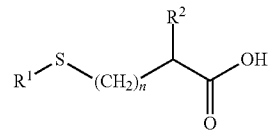

wherein:
  n is an integer from 0 to 2;
  $R^1$ is methyl or ethyl; and
  $R^2$ is selected from the group consisting of hydroxyl and amino.

Other aspects and feature of the invention will be in part apparent and in part pointed out hereinafter.

DETAILED DESCRIPTION OF THE INVENTION

The present invention provides dietary supplements having a balanced mixture of compounds that promote the growth, repair, and maintenance of mammalian bone and joint connective tissue. In accordance, the dietary supplements may be administered to a mammalian subject to treat or prevent several disorders or indications, including but not limited to osteoarthritis, joint effusion, joint erosion, joint inflammation and pain, synovitis, lameness, post operative arthroscopic surgery, deterioration of proper joint function including joint mobility, the reduction or inhibition of metabolic activity of chondrocytes, the reduction or inhibition of enzymes that degrade cartilage, the reduction or inhibition of the production of hyaluronic acid. The dietary supplements may also be administered to a mammalian subject to decrease degradation of articular cartilage or disorders or indications resulting from degradation of articular cartilage. Examples of such disorders or indications are rheumatoid arthritis, psoriatic arthritis, osteoarthrosis, and acute inflammation, such as, e.g., *yersinia* arthritis, pyrophosphate arthritis, and gout arthritis (arthritis urica).

I. Dietary Supplements

The dietary supplements of the invention comprise a combination of at least one metal chelate and at least one chondroprotective agent. Optionally, the dietary supplement may include at least one additional ingredient selected from the group consisting of vitamin, mineral, amino acid, antioxidant, yeast culture, essential fatty acid, and pharmaceutically acceptable excipient. Each of these ingredients is described in detail below.

(a) Metal Chelates

The dietary supplement of the invention comprises at least one metal chelate or a metal salt. In some embodiments, the metal chelate comprises metal ions, and an amino acid ligand or a hydroxy analog thereof. The metal ions may be selected from the group consisting of zinc ions, copper ions, magnesium ions, manganese ions, iron ions, chromium ions, selenium ions, calcium ions and combinations thereof. In a preferred embodiment, the metal ions are zinc ions, manganese ions, and copper ions. The amino acids may be selected from the group comprising alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain embodiments, the copper and zinc ions are preferably divalent, i.e., it carries a charge of $2^+$. The ratio of amino acids to metal ions in the chelate molecule may generally vary from 1:1 to 3:1 or higher. Typically, a metal chelate may comprise a mixture of 1:1, 2:1 and 3:1 species. Preferably, the ratio of amino acids to metal ion in the chelate molecule may generally vary from 1.5:1 to 2.5:1. In an aqueous medium, the relative proportions of these species are determined by the applicable stability constants.

Where the number of ligands equates to the charge on the metal ion, the charge is typically balanced because the carboxyl moieties of the amino acids are in deprotonated form. For example, in the chelate species wherein the metal cation carries a charge of $2^+$ and the amino acid to metal ratio is 2:1, each of the hydroxyl or amino groups is understood to be bound by a coordinate covalent bond to the metal while an ionic bond prevails between each of the carboxylate groups and the metal ion. Where the number of ligands exceeds the charge on the metal ion, e.g., in a 3:1 chelate of a divalent metal ion, the amino acids in excess of the charge typically may remain in a protonated state to balance the charge. On the other hand, where the positive charge on the metal ion exceeds the number of amino acids, the charge may be balanced by the presence of another anion such as, for example, chloride, bromide, iodide, bicarbonate, hydrogen sulfate, dihydrogen phosphate and combinations thereof. Divalent anions may also be present.

In an exemplary embodiment, the metal chelate comprises metal ions and ligands wherein a compound of formula 1 is a source of the ligands. The metal salt comprises metal ions and anions wherein a compound of formula 1 is a source of the anions. The compound of formula 1 has the structure:

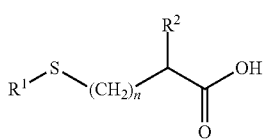

1 wherein:
  n is an integer from 0 to 2;
  $R^1$ is methyl or ethyl; and
  $R^2$ is selected from the group consisting of hydroxyl and amino.

In various embodiments of the present invention, n is 2, $R^1$ is methyl and $R^2$ is hydroxyl (i.e., 2-hydroxy-4-methylthiobutanoic acid). The metal ion may be selected from zinc ions, copper ions, magnesium ions, manganese ions, iron ions, chromium ions, selenium ions, calcium ions and combinations thereof. In an exemplary embodiment, the metal ions are zinc ions, magnesium ions, and copper ions. Where the metal ion is copper, manganese, chromium, calcium, and iron, it is preferably divalent, i.e., it carries a charge of $2^+$.

In an exemplary embodiment, the compound of formula 1 comprises 2-hydroxy-4-methylthiobutanoic acid ("HMTBA"), i.e., n is 2, $R^1$ is methyl and $R^2$ is hydroxyl. In particularly preferred embodiments, the metal ion is copper, zinc, or manganese. Where the metal ion is copper or manganese, it is preferably divalent, i.e., it carries a charge of $2^+$. Zn cations are essentially universally divalent. In other metal chelates useful in the compositions and methods of the invention, the metal ions are also preferably divalent. The ratio of ligands to metal ion in the chelate molecule may generally vary from 1:1 to 3:1 or higher. Typically, a metal chelate may comprise a mixture of 1:1, 2:1 and 3:1 species. Preferably, the ratio of ligands to metal ion in the chelate molecule may generally vary from 1.5:1 to 2.5:1. In an aqueous medium, the relative proportions of these species are determined by the applicable stability constants. In the case where n is 2, $R^2$ is amino and $R^1$ is methyl, i.e., where the compound of formula 1 is methionine, a number of the stability constants are available from the literature. At least some stability constants may also be available for the chelates in which n is 2, $R^2$ is hydroxyl and $R^1$ is methyl, i.e., where the compound of formula 1 is HMTBA.

Where the number of ligands equates to the charge on the metal ion, the charge is typically balanced because the carboxyl moieties of the ligands are in deprotonated form. Thus, in these chelates, each of the ligands corresponds to formula (1A):

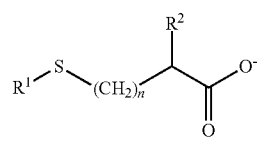

1A wherein $R^1$, $R^2$ and n are as defined above, i.e., the chelate in this respect is also a dicarboxylate salt. For example, in the chelate species wherein the metal cation carries a charge of $2^+$ and the ligand to metal ratio is 2:1, each of the hydroxyl or amino group ($R^2$) groups is understood to be bound by a coordinate covalent bond to the metal while an ionic bond prevails between each of the carboxylate groups and the metal ion. Typical examples are the complexes of $Zn^{2+}$, $Cu^{2+}$, $Mn^{2+}$ with two 2-hydroxy-4-methylthiobutanoate ions. Where the number of ligands exceeds the charge on the metal ion, e.g., in a 3:1 chelate of a divalent metal ion, the ligands in excess of the charge typically may remain in a protonated state to balance the charge. On the other hand, where the positive charge on the metal ion exceeds the number of ligands, the charge may be balanced by the presence of another anion such as, for example, chloride, bromide, iodide, bicarbonate, hydrogen sulfate, dihydrogen phosphate and combinations thereof. Divalent anions may also be present.

Metal salts wherein the metal has a $1^+$ or $2^+$ charge may also be used. These salts form when the metal, metal oxide, metal hydroxide or metal salt (e.g. metal carbonate, metal nitrate or metal halide) reacts with one or more compounds having the structure of Formula 1 to form an ionic bond between the metal and the resulting anion. Generally, these metal salts can be prepared by contacting a metal ion source with HMTBA. Without being bound to a particular theory, it is believed that combinations of Zn, Cu, Mn, Mg, Fe, and Cr, ions with HMTBA are primarily in the form of chelates.

The metal chelates of the present invention can be prepared generally according to the methods described in U.S. Pat. Nos. 4,335,257 and 4,579,962 (each of which is incorporated herein by reference in its entirety).

(b) Chondroprotective Agents

The dietary supplements of the invention include at least one chondroprotective agent. Chondroprotective agents suitable for use in the invention generally improve chondrocyte function. Without being bound to any particular theory, suitable chondroprotective agents may improve chondrocyte function by one or more of the following mechanisms: 1) stimulating chondrocyte synthesis of collagen and proteoglycans, as well as synoviocyte production of hyaluronan; 2) inhibiting cartilage degradation; and 3) preventing fibrin formation in the subchondral and synovial vasculature.

In one embodiment, the chondroprotective agent is glucosamine, or a derivative or salt of glucosamine. Suitable glucosamine forms include glucosamine sulfate, glucosamine hydrochloride, glucosamine hydroiodide, glucosamine pyruvate, glucosamine phosphate, β-glucosamine, α-glucosamine, and N-acetylglucosamine. The daily dosage of glucosamine may range from about 25 to about 3000 mg and more typically, from about 500 to about 1500 mg.

In another embodiment, the chondroprotective agent is chondroitin, or a derivative or salt of chondroitin. Suitable forms of chondroitin include chondroitin chloride, chondroitin bromide, chondroitin sulfate, and chondroitin iodide. The daily dosage of chondroitin may range from about 25 to 3000 mg, and more typically, from about 500 to about 1500 mg.

In yet another embodiment, the chondroprotective agent is hyaluronic acid or a derivative or salt of hyaluronic acid. Suitable salts of hyaluronic acid include the alkali metal salts as well as the alkaline earth metal salts. Typical salts, for example, include sodium hyaluronate, potassium hyaluronate, magnesium hyaluronate and calcium hyaluronate. A typical dosage of hyaluronic acid may range from about 10 to about 2000 mg.

In a further embodiment, the chondroprotective agent is an extract from green-lipped mussel (e.g., *Perna canaliculus*). The daily dosage of such an extract may from about 100 to about 300 mg for a lipid extract or from about 1000 to about 1200 mg of the freeze-dried powder.

In an exemplary embodiment, the chondroprotective agent will comprise a mixture of chondriotin sulfate, hyaluronic acid, glucosamine, and collagen. An exemplary formulation is commercially available under the trade name Natural Egg Shell Membrane (NEM® sold by ESM Technologies, LLC, Carthage, Mo.), which comprises concentrated eggshell membrane.

(c) Vitamins

Optionally, the dietary supplement of the invention may include one or more vitamins. Suitable vitamins for use in the dietary supplement include vitamin C, vitamin A, vitamin E, vitamin B12, vitamin K, riboflavin, niacin, vitamin D, vitamin B6, folic acid, pyridoxine, thiamine, pantothenic acid, and biotin. The form of the vitamin may include salts of the vitamin, derivatives of the vitamin, compounds having the same or similar activity of a vitamin, and metabolites of a vitamin.

The dietary supplement may include one or more forms of an effective amount of any of the vitamins described herein or otherwise known in the art. Exemplary vitamins include vitamin K, vitamin D, vitamin C, and biotin. An "effective amount" of a vitamin typically quantifies an amount at least about 10% of the United States Recommended Daily Allowance ("RDA") of that particular vitamin for a subject. It is contemplated, however, that amounts of certain vitamins exceeding the RDA may be beneficial for certain subjects. For example, the amount of a given vitamin may exceed the applicable RDA by 100%, 200%, 300%, 400% or 500% or more.

(d) Minerals

In addition to the metal chelates or metal salts described in I(a), the dietary supplement may include one or more minerals or mineral sources. Non-limiting examples of minerals include, without limitation, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In an exemplary embodiment, the mineral may be a form of calcium. Suitable forms of calcium include calcium alpha-ketoglutarate, calcium acetate, calcium alginate, calcium ascorbate, calcium aspartate, calcium caprylate, calcium carbonate, calcium chelates, calcium chloride, calcium citrate, calcium citrate malate, calcium formate, calcium glubionate, calcium glucoheptonate, calcium gluconate, calcium glutarate, calcium glycerophosphate, calcium lactate, calcium lysinate, calcium malate, calcium orotate, calcium oxalate, calcium oxide, calcium pantothenate, calcium phosphate, calcium pyrophosphate, calcium succinate, calcium sulfate, calcium undecylenate, coral calcium, dicalcium citrate, dicalcium malate, dihydroxycalcium malate, dicalcium phosphate, and tricalcium phosphate.

Generally speaking, the dietary supplement may include one or more forms of an effective amount of any of the minerals described herein or otherwise known in the art. An "effective amount" of a mineral typically quantifies an amount at least about 10% of the United States Recommended Daily Allowance ("RDA") of that particular mineral for a subject. It is contemplated, however, that amounts of certain minerals exceeding the RDA may be beneficial for certain subjects. For example, the amount of a given mineral may exceed the applicable RDA by 100%, 200%, 300%, 400% or 500% or more. Typically, the amount of mineral included in the dietary supplement may range from about 1 mg to about 1500 mg, about 5 mg to about 500 mg, or from about 50 mg to about 500 mg per dosage.

(e) Essential Fatty Acids

Optionally, the dietary supplement may include a source of an essential fatty acid. The essential fatty acid may be isolated or it may be an oil source or fat source that contains an essential fatty acid. In one embodiment, the essential fatty acid may be a polyunsaturated fatty acid (PUFA), which has at least two carbon-carbon double bonds generally in the cis-configuration. The PUFA may be a long chain fatty acid having at least 18 carbons atoms. The PUFA may be an omega-3 fatty acid in which the first double bond occurs in the third carbon-carbon bond from the methyl end of the carbon chain (i.e., opposite the carboxyl acid group). Examples of omega-3 fatty acids include alpha-linolenic acid (18:3, ALA), stearidonic acid (18:4), eicosatetraenoic acid (20:4), eicosapentaenoic acid (20:5; EPA), docosatetraenoic acid (22:4), n-3 docosapentaenoic acid (22:5; n-3DPA), and docosahexaenoic acid (22:6; DHA). The PUFA may also be an omega-5 fatty acid, in which the first double bond occurs in the fifth carbon-carbon bond from the methyl end. Exemplary omega-5 fatty acids include myristoleic acid (14:1), myristoleic acid esters, and cetyl myristoleate. The PUFA may also be an omega-6 fatty acid, in which the first double bond occurs in the sixth carbon-carbon bond from the methyl end. Examples of omega-6 fatty acids include linoleic acid (18:2), gamma-linolenic acid (18:3), eicosadienoic acid (20:2), dihomo-gamma-linolenic acid (20:3), arachidonic acid (20:4), docosadienoic acid (22:2), adrenic acid (22:4), and n-6 docosapentaenoic acid (22:5). The fatty acid may also be an omega-9 fatty acid, such as oleic acid (18:1), eicosenoic acid (20:1), mead acid (20:3), erucic acid (22:1), and nervonic acid (24:1).

In another embodiment, the essential fatty acid source may be a seafood-derived oil. The seafood may be a vertebrate fish or a marine organism, such that the oil may be fish oil or marine oil. The long chain (20C, 22C) omega-3 and omega-6 fatty acids are found in seafood. The ratio of omega-3 to omega-6 fatty acids in seafood ranges from about 8:1 to 20:1. Seafood from which oil rich in omega-3 fatty acids may be derived include, but are not limited to, abalone scallops, albacore tuna, anchovies, catfish, clams, cod, gem fish, herring, lake trout, mackerel, menhaden, orange roughy, salmon, sardines, sea mullet, sea perch, shark, shrimp, squid, trout, and tuna.

In yet another embodiment, the essential fatty acid source may be a plant-derived oil. Plant and vegetable oils are rich in omega-6 fatty acids. Some plant-derived oils, such as flaxseed oil, are especially rich in omega-3 fatty acids. Plant or vegetable oils are generally extracted from the seeds of a plant, but may also be extracted from other parts of the plant. Plant or vegetable oils that are commonly used for cooking or flavoring include, but are not limited to, acai oil, almond oil, amaranth oil, apricot seed oil, argan oil, avocado seed oil, babassu oil, ben oil, blackcurrant seed oil, Borneo tallow nut oil, borage seed oil, buffalo gourd oil, canola oil, carob pod oil, cashew oil, castor oil, coconut oil, coriander seed oil, corn oil, cottonseed oil, evening primrose oil, false flax oil, flax seed oil, grapeseed oil, hazelnut oil, hemp seed oil, kapok seed oil, lallemantia oil, linseed oil, macadamia oil, meadowfoam seed oil, mustard seed oil, okra seed oil, olive oil, palm oil, palm kernel oil, peanut oil, pecan oil, pequi oil, perilla seed oil, pine nut oil, pistachio oil, poppy seed oil, prune kernel oil, pumpkin seed oil, quinoa oil, ramtil oil, rice bran oil, safflower oil, sesame oil, soybean oil, sunflower oil, tea oil, thistle oil, walnut oil, or wheat germ oil. The plant derived oil may also be hydrogenated or partially hydrogenated.

In still a further embodiment, the essential fatty acid source may be an algae-derived oil. Commercially available algae-derived oils include those from *Crypthecodinium cohnii* and *Schizochytrium* sp. Other suitable species of algae, from which oil is extracted, include *Aphanizomenon flos-aquae, Bacilliarophy* sp., *Botryococcus braunii, Chlorophyceae* sp., *Dunaliella tertiolecta, Euglena gracilis, Isochrysis galbana, Nannochloropsis salina, Nannochloris* sp., *Neochloris oleoabundans, Phaeodactylum tricornutum, Pleurochrysis carterae, Prymnesium parvum, Scenedesmus dimorphus, Spirulina* sp., and *Tetraselmis chui*.

(f) Amino Acids

The dietary supplement may optionally include from one to several amino acids. Suitable amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine or their hydroxy analogs. In certain embodiments, the amino acid will be selected from the essential amino acids. An essential amino acid is generally described as one that cannot be synthesized de novo by the organism, and therefore, must be provided in the diet. By way of non-limiting example, the essential amino acids for humans include: L-histidine, L-isoleucine, L-leucine, L-lysine, L-methionine, L-phenylalanine, L-valine and L-threonine. In an exemplary embodiment, the methionine utilized is a hydroxyl analog of methionine corresponding to Formula (1):

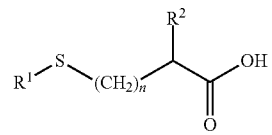

wherein:
n is an integer from 0 to 2;
$R^1$ is methyl or ethyl; and
$R^2$ is selected from the group consisting of hydroxyl and amino.

In an exemplary alternative of this embodiment, n is 2, $R^1$ is methyl and $R^2$ is hydroxyl (i.e., 2-hydroxy-4-methylthiobutanoic acid).

(g) Antioxidants

The dietary supplement may include one or more suitable antioxidants. As will be appreciated by a skilled artisan, the suitability of a given antioxidant will vary depending upon the species to which the dietary supplement will be administered. Non limiting examples of antioxidants include ascorbic acid and its salts, ascorbyl palmitate, ascorbyl stearate, anoxomer, N-acetylcysteine, benzyl isothiocyanate, o-, m- or p-amino benzoic acid (o is anthranilic acid, p is PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, p-coumaric acid, curcurin, 3,4-dihydroxybenzoic acid, N,N'-diphenyl-p-phenylenediamine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eugenol, ferulic acid, flavonoids, flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, propyl gallate, polyphosphates, quercetin, trans-resveratrol, rosmarinic acid, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, zeaxanthin, or combinations thereof.

Natural antioxidants that may be included in the dietary supplement include, but are not limited to, apple peel extract, blueberry extract, carrot juice powder, clove extract, coffeeberry, coffee bean extract, cranberry extract, eucalyptus extract, ginger powder, grape seed extract, green tea, olive leaf, parsley extract, peppermint, pimento extract, pomace, pomegranate extract, rice bran extract, rosehips, rosemary extract, sage extract, tart cherry extract, tomato extract, tumeric, and wheat germ oil.

(h) Anti-Inflammatory Agents

The dietary supplement may optionally include at least one anti-inflammatory agent. In one embodiment, the anti-inflammatory agent may be a synthetic non-steroidal anti-inflammatory drug (NSAID) such as acetylsalicylic acid, dichlophenac, indomethacin, oxamethacin, ibuprofen, indoprofen, naproxen, ketoprofen, mefamanic acid, metamizole, piroxicam, and celecoxib. In an alternate embodiment, the anti-inflammatory agent may be a prohormone that modulates inflammatory processes. Suitable prohormones having this property include prohormone convertase 1, proopiomelanocortin, prohormone B-type natriuretic peptide, SMR1 prohormone, and the like. In another embodiment, the anti-inflammatory agent may be an enzyme having anti-inflammatory effects. Examples of anti-inflammatory enzymes include bromelain, papain, serrapeptidase, and proteolytic enzymes such as pancreatin (a mixture of tyrpsin, amylase and lipase).

In still another embodiment, the anti-inflammatory agent may be a peptide with anti-inflammatory effects. For example, the peptide may be an inhibitor of phospholipase $A_2$, such as antiflammin-1, a peptide that corresponds to amino acid residues 246-254 of lipocortin; antiflammin-2, a peptide that corresponds to amino acid residues 39-47 of uteroglobin; S7 peptide, which inhibits the interaction between interleukin 6 and interleukin 6 receptor; RP1, a prenyl protein inhibitor; and similar peptides. Alternatively, the anti-inflammatory peptide may be cortistatin, a cyclic neuropeptide related to somatostatin, or peptides that corresponds to an N-terminal fragment of SV-IV protein, a conserved region of E-, L-, and P-selectins, and the like. Other suitable anti-inflammatory preparations include collagen hydrolysates and milk micronutrient concentrates (e.g., MicroLactin® available from Stolle Milk Biologics, Inc., Cincinnati, Ohio), as well as milk protein hydrolysates, casein hydrolysates, whey protein hydrolysates, and plant protein hydrolysates.

In a further embodiment, the anti-inflammatory agent may be a probiotic that has been shown to modulate inflammation. Suitable immunomodulatory probiotics include lactic acid bacteria such as acidophilli, lactobacilli, and bifidophilli. In yet another embodiment, the anti-inflammatory agent may be a plant extract having anti-inflammatory properties. Non-limiting examples of suitable plant extracts with anti-inflammatory benefits include blueberries, boswella, black catechu and Chinese skullcap, celery seed, chamomile, cherries, devils claw, eucalyptus, evening primrose, ginger, hawthorne berries, horsetail, *Kalopanax pictus* bark, licorice root, tumeric, white wallow, willow bark, and yucca.

(i) Excipients

A variety of commonly used excipients in dietary supplement formulations may be selected on the basis of compatibility with the active ingredients. Non-limiting examples of suitable excipients include an agent selected from the group consisting of non-effervescent disintegrants, a coloring agent, a flavor-modifying agent, an oral dispersing agent, a stabilizer, a preservative, a diluent, a compaction agent, a lubricant, a filler, a binder, taste masking agents, an effervescent disintegration agent, and combinations of any of these agent.

In one embodiment, the excipient is a binder. Suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof. The polypeptide may be any arrangement of amino acids ranging from about 100 to about 300,000 daltons.

In another embodiment, the excipient may be a filler. Suitable fillers include carbohydrates, inorganic compounds, and polyvinylpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may comprise a non-effervescent disintegrant. Suitable examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In another embodiment, the excipient may be an effervescent disintegrant. By way of non-limiting example, suitable effervescent disintegrants include sodium bicarbonate in combination with citric acid and sodium bicarbonate in combination with tartaric acid.

The excipient may comprise a preservative. Suitable examples of preservatives include antioxidants, such as a-tocopherol or ascorbate, and antimicrobials, such as parabens, chlorobutanol or phenol.

In another embodiment, the excipient may include a diluent. Diluents suitable for use include pharmaceutically acceptable saccharide such as sucrose, dextrose, lactose, microcrystalline cellulose, fructose, xylitol, and sorbitol; polyhydric alcohols; a starch; pre-manufactured direct compression diluents; and mixtures of any of the foregoing.

The excipient may include flavors. Flavors incorporated into the outer layer may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oil, such as lemon oil, orange oil, grape and grapefruit oil, fruit essences including apple, peach, pear, strawberry, raspberry, cherry, plum, pineapple, and apricot.

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; sugar alcohols such as sorbitol, mannitol, sylitol, and the like.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Suitable dispersants may include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

Depending upon the embodiment, it may be desirable to provide a coloring agent in the outer layer. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Taste-masking materials include, e.g., cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcelluose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon® CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking materials contemplated are those described in U.S. Pat. Nos. 4,851,226, 5,075,114, and 5,876,759, each of which is hereby incorporated by reference in its entirety.

In various embodiments, the excipient may include a pH modifier. In certain embodiments, the pH modifier may include sodium carbonate or sodium bicarbonate. In other embodiments, an antioxidant such as BHT or BHA is utilized.

The weight fraction of the excipient or combination of excipients in the dietary supplement may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

(j) Exemplary Formulations

Generally speaking, the dietary supplement may include any of the metal chelates or metal salts described in I(a) in combination with any of the chondroprotective agents described in I(b). Optionally, these dietary supplements may further include any of the ingredients detailed in I(c)(d)(e)(f) (g)(h) or (i). As will be appreciated by a skilled artisan, the type and amount of ingredients forming a given dietary supplement can and will vary greatly depending upon the mammalian subject. The dietary supplement can, in accordance with generally known methods, be formulated to meet the needs of several mammalian subjects. For example, the mammalian subject may be a human, agricultural animal (e.g., cattle, swine, sheep, or goats), zoo animal (e.g., ungulate), or a companion animal (dog, horse, or cat.)

In one exemplary embodiment for a dietary supplement, the metal chelate comprises a mixture of a zinc chelate of 2-hydroxy-4-methylthiobutanoic acid, a manganese chelate of 2-hydroxy-4-methylthiobutanoic acid, and a copper chelate of 2-hydroxy-4-methylthiobutanoic acid; and the chondroprotective agent comprises a mixture of chondriotin sulfate, hyaluronic acid, glucosamine, and collagen. In an exemplary alternative of this embodiment, the chondroprotective agent will comprise NEM®. In each of these embodiments, the dietary supplement may include one to several ingredients selected from the group consisting of vitamins, minerals, amino acids, antioxidants, yeast cultures, anti-inflammatory agents, and essential fatty acids. By way of non-limiting illustration, Example 2 details an exemplary dietary supplement of the invention formulated for a canine, Example 3 details an exemplary dietary supplement of the invention formulated for an equine, and Example 6 details an exemplary dietary supplement of the invention formulated for a human.

It is contemplated, if appropriate, that one or more of the ingredients forming the dietary supplement of the present invention can exist in tautomeric, geometric or stereoisomeric forms without departing from the scope of the invention. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond will each have a hydrogen atom on the same side of the double bond ("cis") or on opposite sides of the double bond ("trans"). Some of the compounds described contain alkenyl groups, and are meant to include both cis and trans or "E" and "Z" geometric forms. Furthermore, some of the compounds described contain one or more stereocenters and are meant to include R, S, and mixtures of R and S forms for each stereocenter present.

Moreover, one or more of the ingredients forming the dietary supplement of the present invention may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the one or more of the corresponding compounds set forth herein.

II. Dietary Supplement Dosage Forms

The dietary supplements detailed herein may be manufactured in one or several dosage forms. In an exemplary embodiment, the dosage form will be an oral dosage form. Suitable dosage forms include a tablet, including a suspension tablet, a chewable tablet, an effervescent tablet or caplet; a pill; a powder such as a sterile packaged powder, a dispensable powder, and an effervescent powder; a capsule including both soft or hard gelatin capsules or non-animal derived polymers, such as hydroxypropyl methylcellulose capsules (i.e., HPMC) or pullulan; a lozenge; a sachet; a sprinkle; a reconstitutable powder or shake; a troche; pellets; granules; liquids; suspensions; emulsions; or semisolids and gels. Alternatively, the dietary supplement may be incorporated into a food product or powder for mixing with a liquid, or administered orally after only mixing with a non-foodstuff liquid. As will be appreciated by a skilled artisan, the dietary supplements, in addition to being suitable for administration in multiple dosage forms, may also be administered with various dosage regimens.

The amount and types of ingredients (i.e., metal chelate, chondroprotective agents, vitamin, mineral, amino acid, antioxidant, yeast culture, and essential fatty acid), and other excipients useful in each of these dosage forms are described throughout the specification and examples. It should be recognized that where a combination of ingredients and/or excipient, including specific amounts of these components, is described with one dosage form that the same combination could be used for any other suitable dosage form. Moreover, it should be understood that one of skill in the art would, with the teachings found within this application, be able to make any of the dosage forms listed above by combining the amounts and types of ingredients administered as a combination in a single dosage form or a separate dosage forms and administered together as described in the different sections of the specification.

The particle size of the active ingredients forming the dietary supplement may be an important factor that can effect bioavailability, blend uniformity, segregation, and flow properties. In general, smaller particle sizes of active ingredients, increases the bioabsorption rate of the active ingredients with substantially poor water solubility by increasing the surface area. The particle size of the active ingredients and excipients can also affect the suspension properties of the dietary supplement. For example, smaller particles are less likely to settle and therefore form better suspensions. In various embodiments, the average particle size of the dry powder of the various ingredients (which can be administered directly, as a powder for suspension, or used in a solid dosage form) is less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In some applications the use of particles less than 15 microns in diameter may be advantageous. In these cases colloidal or nanosized particles in the particle size range of 15 microns down to 10 nanometers may be advantageously employed.

The dietary supplements of the present invention can be manufactured by conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate the invention. In particular, Example 1 demonstrates methods for testing the dietary supplement for safety in horses. Example 2 demonstrates methods for testing the palatability of the dietary supplement in dogs. Examples 3 and 4 present methods for testing the benefits of the dietary supplement for the maintenance and development of healthy joints in mature horses. Example 5 presents a method for testing the therapeutic benefits of the dietary supplement in a rat model of osteoarthritis. Example 5 sets forth an exemplary dietary supplement formulated for a human.

Example 1

Safety of Oral Ingestion of the Dietary Supplement by Mature Horses

The objective of this study was to establish the safety of the oral ingestion of a dietary supplement by mature horses. The dietary supplement comprised dicalcium phosphate, NEM® (natural egg membrane, which comprises glucosamine, chondroitin sulfate, hyaluronic acid, and collagen), ascorbic acid, MHA (methionine hydroxy analog), HMBTA-Mn, HMTBA-Zn, HMBTA-Cu, biotin, Zorien Se, and Vitamin D. A diet containing the dietary supplement was compared to a control diet with respect to the effects on behavioral observations and standard clinical chemistry panels taken using blood samples.

Diets. Two diets were offered to all horses over the course of this study. During the first seven days, all horses were offered a commercial equine diet (control diet) that met or exceeded NRC requirements. During the next fourteen days, the horses were offered the same commercial equine diet with the additional dietary supplement added as a top dress application. The initial rate of administration of dietary supplement was 50 g of dietary supplement for a 500 kg horse. During the final seven days of the study, the horses were offered the original commercial equine diet. A sample of equine feed concentrate was collected weekly. Each batch of dietary supplement was sampled and analyzed for mineral content (Cu, Mn, Zn) as well as for glucosamine, chondroitin, and hyaluronic acid.

Animals and Experimental Design. Five horses (two males, three females) from two locations participated in this study. One male horse and two female horses were stabled at Wehmeyer Farms in Winfield, Mo.; one male and one female horse were stabled at Harrell Farms in Troy, Mo. Each horse was assigned an individual stall to insure intake of the desired amount of dietary supplement. At the completion of the trial, all horses were released from the study.

Behavioral Observations. Animals were observed a minimum of twice daily, and any abnormal observations were recorded.

Blood Samples. Up to ten milliliters of blood were collected from each animal in serum separation tubes and allowed to clot for at least thirty minutes. All samples were spun down for undiluted serum, split into two aliquots and frozen. One aliquot was sent to Antech Veterinary Diagnostic Labs and was analyzed for a standard blood chemistry panel. Blood samples were drawn from all horses at study entry, once every seven days during the study period, and once at the termination of the study.

Data Analysis and Statistics. Blood data was analyzed as paired observations. Differences between the baseline diet blood samples taken during the first two weeks of the study were compared to the experimental diet blood samples taken during the last two weeks of the study, using pdiff procedures of General Linear Models of SAS, and results were presented as a mean value±a standard error of the mean.

Results. The dietary supplement was found to be palatable by all horses in this study, with no significant changes in food intake due to the presence of the dietary supplement. Further, no adverse effects were observed in any of the horses receiving the dietary supplement. The blood chemistry panels all fell within normal ranges for all horses, and no behavioral changes were noted for any horse while the dietary supplement was administered.

Example 2

Palatability of a Canine Treat Comprising the Dietary Supplement

The following study was undertaken to determine the palatability of a dog treat comprising the dietary supplement. Two chewable dog tablets comprising a dietary supplement formulated for canines were manufactured using current Good Manufacturing Practices (cGMPs). One tablet (treat A) was flavored with a chicken digest and the second tablet (treat B) was flavored with a beef and cheese palatant. The dietary supplement comprised MHA, tricalcium phosphate, NEM®, ascorbic acid, HMBTA-Zn, Zorien Se, HMTBA-Cu, HMTBA-Mn, biotin, and Vitamin D.

Animals. Twenty male and female Beagles were housed in a kennel facility registered with the ASDA No. 23-R-126 under the Animal Welfare Act. The kennel had a 12-hour light and 12-hour dark cycle. The temperatures of the kennel were kept with the targeted conditions (i.e., from 50° F. to 85° F.) in accordance with the Animal Welfare Act. Cages and feed bowls were cleaned daily and sanitized in accordance with the Animal Welfare Act.

Experimental Design. Each dog was presented with one of each treats in stainless steel bowls once a day for two days. Bowl placement was reversed each day and both bowls were presented for up to 5 minutes or until the first treat was consumed. Five hours prior to presentation of the treats, each dog was offered 300 g of a standard canine diet (Joy® Special Meal, Joy Pet Food, St. Marys, Ohio) for 30 min. The mean consumption of the canine diet was 85%.

Data Analysis and Statistics. Each dog was identified by ear tattoo and cage number. First approach, first consumption preference, and time (in sec) to consume the first treat were recorded each day for each dog. Chi-square and t test analyses were used to analyze the data.

Results. Table 1 presents the first approach preference and first consumption preference of each dog for the two trials. It was found that the dogs approached both treats about equally, but that they consumed treat A about nine times more frequently than treat B.

TABLE 1

Summary of Dog Treat Palatability.

| Dog | First Approach | | First Consumption | |
|---|---|---|---|---|
|  | Treat A | Treat B | Treat A | Treat B |
| 1 | 1 | 1 | 2 | 0 |
| 2 | 1 | 1 | 1 | 1 |
| 3 | 1 | 1 | 2 | 0 |
| 4 | 1 | 1 | 2 | 0 |
| 5 | 1 | 1 | 1 | 1 |
| 6 | 2 | 0 | 2 | 0 |
| 7 | 1 | 1 | 2 | 0 |
| 8 | 1 | 1 | 2 | 0 |
| 9 | 1 | 1 | 1 | 1 |
| 10 | 1 | 1 | 2 | 0 |
| 11 | 1 | 1 | 1 | 1 |
| 12 | 1 | 1 | 2 | 0 |
| 13 | 2 | 0 | 2 | 0 |
| 14 | 2 | 0 | 2 | 0 |
| 15 | 1 | 1 | 2 | 0 |
| 16 | 1 | 1 | 2 | 0 |
| 17 | 1 | 1 | 2 | 0 |
| 18 | 1 | 1 | 2 | 0 |
| 19 | 1 | 1 | 2 | 0 |
| 20 | 1 | 1 | 2 | 0 |
| Total | 23 | 17 | 36 | 4 |

Among all the dogs, treat A was the first approached preference 23 times and treat B was the first approached preference 17 times. At the level of individual dogs, treat A was the first approach preference for 3 dogs (15%), treat B was the first approach preference for 0 dogs, and both treats A and B were approached equally by 17 dogs (85%). Chi square analysis found no statistical significance in the first approach preference. Similarly, t-test analysis found no statistical significance in the first approach preference at the 95% level of significance. The P-value was 0.08281.

Overall, treat A was the first consumption preference 36 times and treat B was the first consumption preference 4 times. At the level of individual dogs, 16 dogs (80%) consumed treat A on both days, no dogs consumed treat B on both days, and 4 dogs (20%) consumed treat A one day and treat B the other day. Chi square analysis found a statistical significant difference in the first consumption preference. Similarly, t-test analysis found a statistical significant difference in the first consumption preference at the 95% level of significance. The P-value was 0.00000. The time it took to consume the treats ranged from 3 sec to 190 sec. Because there were so few instances of consumption of treat B, a statistical analysis was not possible.

This study revealed that dogs prefer chicken flavored tablets comprising the dietary supplement.

Example 3

Detection of Joint Diseases and Therapeutic Benefits of the Dietary Supplement in Horses The first objective of this study is to monitor equine urine and/or plasma/serum levels of cartilage and synovium metabolism markers, as well as markers for inflammation and oxidative stress, in order to establish mean levels and variance within and across individuals and to look for patterns that may correspond to joint pathology. The second objective of the study is to test the benefits of the dietary supplement as a potential alternative treatment for horses with joint diseases.

The study will comprise two groups of horses that will receive the dietary supplement for the same period of time. The two groups will differ in the periods of time they are monitored before and after treatment. The equine dietary supplement is described above in Example 1.

Animals. Mature domestic horses (*Equus cabalbus*) at least 2 years of age will be included in the study. Horses that have had joint surgery in the previous 120 days will be excluded. Horses will also be excluded if they have had 1) systemic glycosaminoglycans (GAGs) in the previous 30 days, 2) dietary vitamin, mineral, or joint health supplements in the previous 14 days, 3) systemic steroids in the previous 7 days, or 4) systemic non-steroidal anti-inflammatory drugs (NSAIDs) in the previous 7 days. An equine veterinarian will assess the general health of each horse prior to the start of the study using both the previous medical history and a physical examination. An equine veterinarian will evaluate joint condition and assign a lameness score using the American Association of Equine Practitioners (AAEP) lameness scale (see, for example, http://www.aaep.org). Horses will be given ad libitium access to water, and will continue to be fed and exercised as before the trial.

Experimental Design. After the initial lameness scoring, the horses will be randomly assigned to either group A or group B, such that both groups have approximately the same number of horses and are approximately matched for age and lameness scores. The trial may comprise 4 periods, as diagramed in Table 2. Periods 1 and 4 are pretreatment and posttreatment periods, respectively, and Periods 2 and 3 are treatment periods during which one of the groups is treated and the other is not. In Table 2, "0" indicates no treatment, and "T" indicates treatment. During the treatment periods, the dietary supplement may be administered at a dose of 50 grams per animal per day. The supplement may be mixed into the daily feed ration.

TABLE 2

Experimental Design.

| Group | Period 1 (4 weeks) | Period 2 (8 weeks) | Period 3 (8 weeks) | Period 4 (4 weeks) |
|---|---|---|---|---|
| A | 0 | T | 0 | 0 |
| B | 0 | 0 | T | 0 |

Prior to the start of Period 1, any drug and/or supplement administration will be terminated, and the general health of each animal will be assessed, as detailed above. Table 3 presents the detailed schedule for the four periods of the trial.

TABLE 3

Experimental Protocol.

| | Collect blood, urine, and thermal images | Determine AAEP lameness score |
|---|---|---|
| Pre-trial | | day 0 |
| Period 1 (28 days) | days 1, 14, 28 | day 28 |
| Period 2 (56 days) | days 3, 7, 14, 28, 42, 56 | days 28, 56 |
| Period 3 (56 days) | days 3, 7, 14, 28, 42, 56 | days 28, 56 |
| Period 4 (28 days) | days 14, 28 | day 28 |

Blood Collection. Blood may be collected from the jugular vein and placed into two separate tubes for serum and plasma collection. The samples may be frozen at −20° C. until analyzed. Plasma and/or serum may be assayed for biomarkers of cartilage metabolism (e.g., PIIANP, CTX-II, COMP), as well as markers for inflammation (e.g., IL-6) or oxidative stress (e.g., 8-iso-PGF$_{2\alpha}$, PGE2). Vitamin D, Vitamin E, ascorbic acid, zinc, copper, and manganese serum levels may also be measured.

Urine Collection. Urine may be collected using free flow collection and frozen at −20° C. until analyzed. Urine may be analyzed for glycosyl-galactosyl-pyridinoline (a marker of synovial metabolism) and CTX-II. All biomarker levels from urinary assays will be corrected by the urinary creatinine concentration.

Thermal Imaging. Thermal images may be taken with a FLUKE thermal imager system (Fluke Corp., Everett, Wash.) in accordance with the manufacturer's instructions. Images may be taken of the whole animal from the anterior, the posterior, and both sides. Images may also be taken of specific regions of inflammation. Both the ambient temperature and the body temperature of the animal may be recorded at the time of imaging. In general, images will be taken immediately before the collection of other samples.

Concurrent Therapies. Certain therapies (e.g., GAGs, steroids, NSIADs, and other supplements) will be prohibited during the trial. Other therapies will be evaluated by a veterinarian on a case-by-case basis and will be allowed if they are not believed to effect levels of the selected biomarkers. All concurrent therapies will be recorded. In addition, horses may not receive acupuncture, massage, chiropractic treatment during the course of the trial.

Data Analysis. The concentration of a biomarker may be presented as a mean value±a standard deviation. Statistical differences may be determined using a Student's t test. Analysis of the biomarkers during Period 1 may be used to establish inter- and intra-individual variance over time using age and lameness as dependent variables. Patterns of the biomarkers detected during Period 1 may correspond to joint pathology. Changes in the patterns or concentrations of biomarkers and/or or changes in the lameness scores and/or changes in the thermal images may be detected as a consequence of the treatment with the dietary supplement.

If concentrations of select biomarkers decrease and/or lameness scores decrease as a consequence of treatment with the dietary supplement, it may be concluded that the dietary supplement provides therapeutic benefits for the treatment of joint disease in horses. The therapeutic benefit may be manifested by relief of pain associated with joint disease, and/or the growth, repair, and/or maintenance of joint tissue.

Example 4

Therapeutic Benefits of the Dietary Supplement in Horses with Joint Diseases The objective of the following study is to determine whether treatment of horses having a history of lameness with the dietary supplement aids in the control of clinical signs associated with joint health (i.e., reduces lameness scores, alleviates the symptoms of joint disease, stabilizes or prevents further deterioration of joint tissue, and/or promotes the growth and/or repair of joint tissue.)

A double-blind placebo-controlled study will compare two groups: one group will be fed the test dietary supplement, and the second group will be fed a comparable dietary supplement that does not contain the active ingredients. The equine dietary supplement is detailed above in Example 1.

Animals. Mature domestic (privately owned) horses at least 2 years of age with joint health problems will be included in the study. Joint health problems include joint effusion, lameness or other clinical signs common to degenerative joint disease or osteoarthritis. To be included, horses will have an AAEP lameness score equal to or greater than 2.0 and less than 4.0. If bi-lateral lameness is evident, the more severely affected limb will be declared the affected limb. Horses that had joint surgery in the previous 120 days will be excluded. Horses will also be excluded if they have had 1) intraarticular injections in the affected joints in the previous 90 days, 2) systemic GAGs in the previous 30 days, 3) dietary vitamin, mineral, or joint health supplements in the previous 14 days, 4) systemic steroids in the previous 7 days, 5) systemic non-steroidal anti-inflammatory drugs (NSAIDs) in the previous 7 days, or 6) changes in shoeing or trimming in the previous two weeks. Horses will be given ad libitium access to water, and feed (hay, and if necessary, grain) will be offered to maintain body weight.

Animals may be subjected to a 21-day adaptation phase before the start of the trial. The animals may undergo an initial evaluation by an equine veterinarian.

Experimental Design. The study will comprise a randomized complete block design, with horses blocked by lameness grade and affected joint. Within each block (pair), horses will be randomly assigned to either control or treatment groups. The control group will receive placebo dietary supplement (i.e., alfalfa meal, molasses, and flax oil). The treatment group may be dosed at 50 g of dietary supplement per animal per day. The dietary supplements may be mixed into the feed. If a horse fails to consume the feed or the supplement separates from the feed and is not completely consumed, the feed may be moistened with water or molasses to enhance palatability and discourage separation. The clinical investigator will be blinded as to treatment assignment to ensure that all observations are recorded in an unbiased manner.

The duration of the study may be six weeks (42 days). Table 4 presents the study schedule.

TABLE 4

Study Activities.

| Study Day | Activity |
|---|---|
| Day −21 | Veterinary baseline evaluation. |
| Day 0 (±2 days) | History, owner permission, veterinary evaluation, block and assign treatments, synovial fluid, serum collection |
| Days 14, 28, 42 (±2 days) | Veterinary evaluation, serum, synovial fluid collection |

General Veterinary Evaluation. Previous evaluations of the same horse may not be consulted. The affected limb and the contra-lateral limb generally will be scored separately for AAEP lameness grade and only the affected limb for the remainder of the parameters. However, if the horse demonstrates bilateral lameness on any evaluation day, both limbs will be scored for all parameters. Visual analog scale (VAS) parameters may be marked using a vertical line indicating the appropriated spot on the 10 cm line.

Lameness Scores. Lameness may be assessed using the AAEP lameness grading scale. The data form includes a description of the footing used during the evaluation. The footing may not be changed for each horse for the duration of the study.

Lameness at Walk (VAS). Lameness of the affected limb at the walk may be scored on a 10 cm Visual Analog Scale (VAS) where the left hand side pertains to soundness at the walk and the right hand side pertains to non-weight bearing.

Lameness at Trot (VAS). Lameness of the affected limb at the trot may be scored on a 10 cm Visual Analog Scale (VAS) where the left hand side pertains to soundness at the trot and the right hand side pertains to non-weight bearing.

Stride Length. The affected limb may be picked up, the hoof cleaned and sprayed with water. Colored chalk (powdered) may be applied to the bottom of the hoof and the horse will be trotted on a surface suitable to visualize the hoof strike marks (e.g. concrete or pavement). Measuring from the most distal mark visible, stride length may be measured using a tape measure. A minimum of 3 and a maximum of 6 strides may be recorded in feet and inches.

Joint Flexion. The affected joint may be gently flexed to the highest degree possible with little or no resistance. Flexion may be scored on a 10 cm VAS where 0= normal and 10=no flexion. If the affected joint (e.g.) pastern, coffin and navicular) has inherent limited mobility, this measurement cannot be taken and "NA" will be entered onto the data form for "not-applicable".

Response to Joint Flexion. The horse's response to joint flexion may be scored on a 10 cm VAS where 0=normal and 10=extreme response (provided the affected joint is one that can be flexed, see above).

Lameness After Joint Flexion. The affected joint may be held in a flexed position for 60 seconds and the horse trotted immediately upon release of the flexed joint. Lameness may be measured on a 10 cm VAS where 0=normal and 10=non-weight bearing.

Quality of Life Index. Quality of life may be assessed using all of the above parameters, as well as, the horse's demeanor on a 10 cm VAS where 0=excellent quality of life no obvious discomfort associated with DJD and 10=poor quality of life.

Synovial Fluid. Following veterinary evaluation, the affected joint may be cleaned externally (clipped if necessary) and a sample of synovial fluid may be collected aseptically into a EDTA-containing tube. Synovial fluid may be assayed for WBC, total protein, osteocalcin, IL-6, and TNFα.

Blood. Blood may be collected using a heparinized syringe and tube and centrifuged for plasma. Plasma may be assayed for bone and cartilage markers (e.g., osteocalcin, DPD, calcitonin, COMP, CTX-II, PIIANP) as well as measures of inflammation (e.g., cytokines such as IL-1β, Il-6, TNFα, 8-iso-PGF2α, iNOS, COX-2).

Removal of Subjects from the Study. Horses may be removed from the study in the event of a serious health event, with complete documentation of the health event and any treatments administered. Horses may not be removed by the investigator except on a case-by-case basis upon consultation with sponsor and study monitor.

Concurrent Therapies. Therapeutic intervention to treat medical conditions may be necessary during the course of the study because the test animals are privately owned. The health and well being of the individual horse will be the highest priority of the investigator, owner/trainer, and any other attending veterinarian. Use of intra-articular therapies into the affected joint, systemic therapy with PSGAGs or hyaluronic acid, treatment with NSAIDs or corticosteroids, or initiation of dietary supplements(s) for joint health (e.g. glucosamine, chondroitin sulfate, MSM, perna mussel) is prohibited during this study and will result in elimination of the horse from the study. Sporadic use of medications for other disease processes must be evaluated on a case-by-case basis to determine if the horse may remain in the data set or must be eliminated. Clinical assessment of the horse as per protocol may not be performed within 7 days of NSAID administration. Owners/trainers should not permit acupuncture, massage, chiropractic or other alternative modalities on study horses during the experimental period. All concurrent medications and dietary supplements will be documented. During the study, horses may be trimmed/shod; however no changes in the trimming or shoeing pattern will be permitted (i.e. angles, shoe types, addition/deletion or pads). Horses may not undergo dramatic changes in exercise schedules during the study.

Data Analysis. Horses will be classified as responders if their AAEP lameness score decreases by 1 or more units at the end of treatment or if one of the lameness VAS decreases by 2 or more cm. The number of responders and non-responders from each treatment group will be compared. Means and standard deviations of all parameters will also be determined.

Example 5

Effectiveness of Dietary Supplement in Rat Osteoarthritis Model

The objective of this study is to determine whether the dietary supplement reduces the severity of osteoarthritis in the monosodium iodoacetate (MIA) rat model of osteoarthritis.

Experimental Design. The study may comprise three groups of rats: 1) a control group with no dietary supplement, 2) a group provided with the equine dietary supplement (as detailed above), and 3) a group supplemented with NEM (i.e., glucosamine, chondroitin sulfate, hyaluronic acid, and collagen). In general, the rats will be male Wistar rats of about 250-300 g, with 16 rats per group. The rats may undergo a month-long pre-trial period. For the study, each rat will be injected with MIA in the right knee and saline in the left knee, fed one of the three diets, and monitored for 56 day. Table 5 present the study schedule.

TABLE 5

Rat Study Schedule.

| Study day | Activity |
| --- | --- |
| Day −28 | One month pre-feed. Rats will be fed a typical rat diet; treatments 2 & 3 will be fed the identical diet, but with the test supplement incorporated into the diet. |
| Day 0 | Allot rats to one of three groups. Inject monosodium iodoacetate (MIA) into right infrapatellar knee ligament; saline into left knee. |
| Day 1 | Take thermal image of both left and right knees from each rat. Assess hind paw leg distribution. |
| Day 3 | Take thermal image of both left and right knees from each rat. Assess hind paw leg distribution. |
| Day 5 | Take thermal image of both left and right knees from each rat. Assess hind paw leg distribution. |
| Day 7 | Take thermal image of both left and right knees from each rat. Assess hind paw leg distribution. Anesthetize four rats from each group (12 total); collect blood, joint swelling measurements & collect for histology. (36 remaining) |
| Day 10 | Take thermal image of both left and right knees from each rat. Assess hind paw leg distribution. |
| Day 14 | Take thermal image of both left and right knees from each rat. Assess hind paw leg distribution. Anesthetize four rats from each group (12 total); collect blood, joint measurements for swelling and collect for histopathology (24 remaining). |
| Day 21 | Take thermal image of both left and right knees from each rat. Assess hind paw leg distribution. |
| Day 28 | Take thermal image of both left and right knees from each rat. Assess hind paw leg distribution. Anesthetize four rats from each group (12 total). Collect blood, joint measurements for swelling and collect for histopathology (12 remaining. |
| Day 56 | Take thermal image of both left and right knees from each rat. Assess hind paw leg distribution. Anesthetize remaining rats (12). Collect blood, joint measurements for swelling and collect for histopathology. |

Joint Swelling. Joint swelling may be measured by calipers. Alternatively, thermal imaging may also be useful for quantifying swelling. Rats will be lightly anesthetized with isoflurane before measuring.

Blood. Blood may be collected on anesthetized rats using isoflurane anesthesia via cardiac puncture using a heparinized syringe and tube, centrifuged for plasma, and frozen until analysis. Samples may be analyzed for biomarkers of cartilage and bone metabolism (PIIANP, CTX-II, COMP, osteocalcin), and measures of inflammation (IL-6, IL-1β).

Thermal Imaging. The FLUKE Thermal Imaging system may be used to image rats on the indicated days. The left and right knee will be evaluated in the same image. Environmental temperature will also be recorded.

Histology. Samples may be stained with H&E, Safranin O, and Toluidine Blue stains to detect bond histopathology, as well as cartilage and bone biomarkers.

Incapacitance Testing. The incapacitance tester yields an estimate of hind paw weight distribution analysis. This measurement may provide a quantitative measurement of mobility and pain. The MIA-injected knee should be more painful, therefore more weight should be distributed on the saline-injected knee.

Data Analysis. The various indicators may be presented as means and standard deviations. It is expected that all animals may show signs of inflammation and swelling at the early time points (soon after injection), while bone degradation and synthesis may occur at later time points. Differences in the responses of the treated groups versus the control group may indicate that the treatment alleviated the symptoms associated with osteoarthritis and/or prevented the development of osteoarthritis.

Example 6

Human Formulation

A HPMC capsule comprising a dietary supplement formulated for a human was manufactured using current Good Manufacturing Practices (cGMPs). The human dietary supplement comprises calcium (as eggshell calcium), magnesium (as magnesium oxide), HMTBA-Zn, Vitamin C, NEM®, HMTBA-Mn, HMTBA-Cu, Zorien Se, Vitamin K, and Vitamin D.

What is claimed is:

1. A dietary supplement comprising at least one chondroprotective agent and at least one metal chelate; the metal chelate comprising at least one metal ion and at least one ligand, the ligand comprising a compound having formula (1):

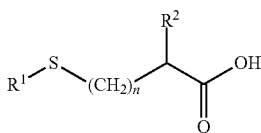

wherein:
n is an integer from 0 to 2;
$R^1$ is methyl or ethyl; and
$R^2$ is selected from the group consisting of hydroxyl and amino;
wherein the average ligand to metal ion ratio is from about 1:1 to about 3:1; and,
wherein the metal chelate comprises a mixture of a zinc chelate of 2-hydroxy-4-methylthiobutanoic acid, a manganese chelate of 2-hydroxy-4-methylthiobutanoic acid, and a copper chelate of 2-hydroxy-4-methylthiobutanoic acid;
and the chondroprotective agent comprises concentrated eggshell membrane.

2. The dietary supplement of claim 1, further comprising at least one ingredient selected from the group consisting of vitamin, mineral, amino acid, antioxidant, yeast culture, anti-inflammatory agent, and essential fatty acid.

3. The dietary supplement of claim 1, wherein the metal ions are selected from the group consisting of zinc ions, copper ions, manganese ions, magnesium ions, iron ions, chromium ions, calcium ions, and combinations thereof.

4. The dietary supplement of claim 1, wherein the metal ions are selected from the group consisting of manganese ions, zinc ions, and copper ions, and the ligand is 2-hydroxy-4-methylthiobutanoic acid.

5. The dietary supplement of claim 1, further comprising at least one ingredient selected from the group consisting of vitamin, mineral, amino acid, antioxidant, yeast culture, anti-inflammatory agent, and essential fatty acid.

6. The dietary supplement of claim 1, further comprising vitamin C, biotin, vitamin D, selenium, calcium, phosphate, and 2-hydroxy-4-methylthiobutanoic acid.

7. The dietary supplement of claim 6, further comprising dried molasses, flax oil, yeast culture, and alfalfa meal.

8. The dietary supplement of claim 1, further comprising magnesium, vitamin C, vitamin K, selenium, calcium, and vitamin D.

9. The dietary supplement of claim 1, wherein the dietary supplement has from about 2% to about 20% by weight metal chelate and from about 5% to about 40% by weight chondroprotective agent.

10. A method for promoting at least one of pain relief, growth, repair, and/or maintenance of bone and/or joint tissue in a mammalian subject, the method comprising administering to the mammalian subject a dietary supplement comprising at least one chondroprotective agent and at least one metal chelate; the metal chelate comprising at least one metal ion and at least one ligand, the ligand comprising a compound having formula (1):

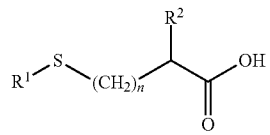

wherein:
n is an integer from 0 to 2;
$R^1$ is methyl or ethyl; and
$R^2$ is selected from the group consisting of hydroxyl and amino;
wherein the average ligand to metal ion ratio is from about 1:1 to about 3:1; and,
wherein the metal chelate comprises a mixture of a zinc chelate of 2-hydroxy-4-methylthiobutanoic acid, a manganese chelate of 2-hydroxy-4-methylthiobutanoic acid, and a copper chelate of 2-hydroxy-4-methylthiobutanoic acid;
and the chondroprotective agent comprises concentrated eggshell membrane.

11. The method of claim 10, further comprising at least one ingredient selected from the group consisting of vitamin, mineral, amino acid, antioxidant, yeast culture, anti-inflammatory agent, and essential fatty acid.

12. The method of claim 10, wherein the metal ions are selected from the group consisting of zinc ions, copper ions, manganese ions, magnesium ions, iron ions, chromium ions, calcium ions, and combinations thereof.

13. The method of claim 10, wherein the metal ions are selected from the group consisting of manganese ions, zinc ions, and copper ions, and the ligand is 2-hydroxy-4-methylthiobutanoic acid.

14. The method of claim 10, further comprising at least one ingredient selected from the group consisting of vitamin, mineral, amino acid, antioxidant, yeast culture, anti-inflammatory agent, and essential fatty acid.

15. The method of claim 10, wherein the mammalian subject is an equine or companion animal, and further comprising vitamin C, biotin, vitamin D, selenium, calcium, phosphate, and 2-hydroxy-4-methylthiobutanoic acid.

16. The method of claim 15, wherein the mammalian subject is an equine, and further comprising dried molasses, flax oil, yeast culture, selenium, and alfalfa meal.

17. The method of claim 15, wherein the mammalian subject is a canine, and further comprising brewer's yeast and a flavor excipient.

18. The method of claim 10, wherein the mammalian subject is a human; and further comprising magnesium, vitamin C, vitamin K, selenium, calcium, and vitamin D.

19. The method of claim 10, wherein the dietary supplement has from about 2% to about 20% by weight metal chelate and from about 5% to about 40% by weight chondroprotective agent.

20. The method of claim 10, wherein the mammalian subject is selected from the group consisting of companion animals, zoo animals, and humans.

21. The method of claim 10, wherein the mammalian subject has a joint-related indication.

22. The method of claim 21, wherein the joint-related indication is selected from the group consisting of osteoarthritis, rheumatoid arthritis, psoriatic arthritis, joint effusion, joint inflammation and/or pain, synovitis, lameness, post operative arthroscopic surgery, deterioration of proper joint function, the inhibition of metabolic activity of chondrocytes, and the inhibition of the production of hyaluronic acid.

23. The dietary supplement of claim 1, wherein the metal chelate comprises at least two metal ions.

24. The method of claim 10, wherein the metal chelate comprises at least two metal ions.

* * * * *